United States Patent [19]

Kricka et al.

[11] Patent Number: 4,598,044

[45] Date of Patent: Jul. 1, 1986

[54] ENHANCED LUMINESCENT OR LUMINOMETRIC ASSAY

[75] Inventors: Larry J. Kricka; Gary H. G. H. Thorpe, both of Birmingham; Thomas P. Whitehead, Leamington Spa, all of England

[73] Assignee: National Research Development Corporation, London, England

[21] Appl. No.: 578,783

[22] Filed: Feb. 9, 1984

[30] Foreign Application Priority Data

Feb. 11, 1983 [GB] United Kingdom ................ 8303820
Apr. 20, 1983 [GB] United Kingdom ................ 8310721

[51] Int. Cl.$^4$ .................. G01N 33/53; G01N 33/564; C12Q 1/66; C12Q 1/28
[52] U.S. Cl. .......................................... 435/28; 435/7; 435/8; 435/810; 436/508; 436/531; 436/800; 436/817; 544/234; 544/237
[58] Field of Search ..................... 435/7, 8, 28, 810; 544/234, 237; 436/800, 817, 508, 531

[56] References Cited

U.S. PATENT DOCUMENTS

| 4,104,029 | 8/1978 | Maier, Jr. | 435/7 |
| 4,302,534 | 11/1981 | Halmann et al. | 435/8 |
| 4,521,511 | 6/1985 | Stout | 435/28 |

FOREIGN PATENT DOCUMENTS

| 0054358A | 6/1982 | European Pat. Off. |
| 0070686 | 1/1983 | European Pat. Off. |
| 2383441 | 10/1978 | France |
| 2008247B | 5/1979 | United Kingdom |
| 2026690A | 2/1980 | United Kingdom |
| 2070768A | 9/1981 | United Kingdom |

OTHER PUBLICATIONS

Chemical Abstracts I: 93: 64280u, pp. 239-257, Proc.—Int. Symp. Anal. Appl. Biolumin. Chemilumin., 1978.
Chemical Abstracts II: 94: 78959e (9), pp. 233-243, Bull. Liaison—Groupe Polyphenols, 1980.
D. F. Roswell et al., in "Methods in Enzymology", vol. LV11, 416 & 417 (1978).
K. D. Gundermann et al., in "Luminescent Assays: Perspectives in Endocrinology and Clinical Chemistry", ed. M. Serio and M. Pazzagli, Raven Press, New York, 1982, pp. 157-161.
T. P. Whitehead et al., Clinical Chemistry 25, 1531-1546 (1979).
F. McCapra, Progess in Organic Chemistry 8, Chapter 6, pp. 248-251 (1973).
A. P. Wagner et al., Analytical Biochemistry 129, 326-328 (1983).
N. N. Ugarova et al., translated from Biokhimiya 43, 1731-1742 (1978).
Sigma Chemical Co., Ltd. catalogue, Feb. 1985, pp. 792-794.
D. Slawinska et al., Proc. Int. Symp. Anal. Appl. Biolumin. Chemilumin. 1978, edited by E. Schram and P. Stanley, State Print & Publ. Inc., Westlake Village, California, USA, 1979, pp. 239-257.
"Heterocyclic Compounds", ed. R. C. Elderfield, John Wiley & Sons, Inc., vol. 6, Chapter 6, pp. 228-230.
J. R. Whitaker et al., Biochim. Biophys. Acta 62, 310-317 (1962).
I. Fridovich, J. Biol. Chem. 238, 3921-3927 (1963).
W. Straus, Journal of Histochem. Cytochem. 30, 491-493 (1982).
B. Chance, Arch. Biochem. Biophys. 41, 389-410 (1952).
I. Yamazaki, "Free Radicals in Biology", vol. III, Ed. W. A. Pryor, Academic Press, New York, 1977, Chapter 5, pp. 183-218.
I. Yamazaki et al., Biochim. Biophys. Acta 77, 47-64 (1963).
S. J. Klebanoff, J. Biol. Chem. 234, 2437-2442 (1959).
I. Aviram, Arch. Biochem. Biophys. 212, 483-490 (1981).
L. Sasson et al., Arch. Biochem Biophys. 217, 529-535 (1982).
Anon., Research Disclosure No. 16034, 19-24 Aug. 1977.
D. J. Capaldi et al., Anal. Biochem. 129, 329-336 (1983).
C. C. Allain et al., Clinical Chemistry 20, 470-475 (1974).
Eiken Chemical Ltd., Chemical Abstract 94, 135589k (1981).
P. Fossati et al., Clinical Chemistry 26, 227-231 (1980).
D. Barham et al., Analyst 97, 142-145 (1972) Abstract.
F. Meittini, Chemical Abstract 89, 208632c (1978).
Kureha Chemical Industry Co. Ltd., Chemical Abstract 94, 1791m (1981).
Kureha Chemical Industry Co. Ltd., Chemical Abstract 94, 1792n (1981).
Y Avi—Dor et al., Chemical Abstract 49, 5559f (1955).
K. Matsuoka et al., Chem. Pharm. Bull. 27, 2345-2350 (1979).
S. D. Lidofsky et al., Proc. Nat. Acad. Sci. USA 78, 1901-1905 (1981).
K. Zaitsu et al., Anal. Biochem. 109, 109-113 (1980).
J. Lobarzewski et al., Annales Universitatis Mariae Curie-Sklodowska Lublin Polania 27, Section C, 87-98 (1972).
I. Kozlik, Chemical Abstract 95, 215703d (1981).
C. R. Lyttle et al., Biochem J 127, 481-487 (1972).
A. Mucchielli et al., Biochem. Biophys. Res. Comm. 94, 894-900 (1980).
M. Halmann et al., Photochemistry and Photobiology 30, 165-167 (1979).
G. Ahnstrom et al., Acta. Chem. Scand 19, 313-316 (1965).

*Primary Examiner*—David M. Naff
*Assistant Examiner*—Louanne C. Krawczewicz
*Attorney, Agent, or Firm*—Murray and Whisenhunt

[57] ABSTRACT

A phenolic compound is used to enhance the sensitivity of a luminescent reaction such as carried out in an immunoassay between a peroxidase enzyme, an oxidant, and a chemiluminescent 2,3-dihydro-1,4-phthalazinedione. Preferably, the phenolic compound is 4-iodophenol, 4-phenylphenol or 2-chloro-4-phenylphenol. In the preferred embodiment, horseradish peroxidase is coupled to an antibody to the substance to be assayed.

15 Claims, No Drawings

ENHANCED LUMINESCENT OR LUMINOMETRIC ASSAY

The present invention relates to an enhanced luminescent or luminometric assay, particularly immunoassay, and to a diagnostic kit designed to facilitate the assay.

Immunoassay is one of the most widely used analytical techniques in the clinical laboratory. At present the majority of immunoassays employ a radioactive isotope, especially iodine-125, as a label. However radioactive istopes have a number of major disadvantages. First, the method of labelling involves the use of highly radioactive and hence potentially hazardous agents. Second, the shelf life of the radioactively labelled substance is often relatively short, not only because by its very nature the radioactive isotope is continuously decaying but also because radioactively labelled proteins are often unstable. Third, it is often difficult to label proteins sufficiently to provide a sensitively and rapidly detectable reagent. Fourth, the disposal of radioactively labelled substances is inconvenient.

These disadvantages have stimulated a search for viable alternatives to the radiolabel. To be suitable as a label a substance should meet at least the following three requirements:
a. it should be detectable both rapidly and in very small quantities when attached to a ligand such as an antigen or an antibody:
b. it should be possible to attach it, without affecting its determination, to a ligand such as an antigen or an antibody, and
c. once attached, it should not significantly alter the properties of the ligand.

Some of the most promising alternative labels are either substances which can themselves take part in a reaction resulting in the emulsion of luminescent light or substances which, on suitable treatment, product compounds capable of taking part in a luminescent reaction. The luminescent reaction (a chemical reaction that results in the emission of luminescent light) is generally of sufficient duration to enable the light emitted to be detected and measured, and thereby to allow the quantification of the labelled material. On the other hand the measurement of luminescence is a rapid process and may be completed in a matter of seconds rather than the several minutes generally required for the measurement of radioactivity.

Luminescence has been employed in three major luminescent or luminometric immunoassay systems:
a. Organoluminescent or organoluminometric immunoassays wherein chemiluminescent or bioluminescent compounds which participate directly in luminescent reactions (ie which are converted to an excited state and then return to a non-excited state with the emission of a photon) have been used to label ligands such as proteins, hormones, haptens, steroids, nucleic acids, metabolites, antigens and/or antibodies. Examples of suitable compounds include luminol and isoluminol;
b. Luminescent catalyst or cofactor immunoassays wherein catalysts or cofactors of luminescent reactions have been used as labels. An example of a suitable catalyst is the enzyme peroxidase; and
c. Enzyme-linked immunoassays wherein luminescent reactions have been used to determine the products formed by the action of enzyme labels on suitable substrates. An example of this type of immunoassay is the determination of antibody linked glucose oxidase by reacting the enzyme/antibody reagent with glucose to form hydrogen peroxide and then measuring the amount of hydrogen peroxide produced by adding luminol under controlled conditions to initiate a luminescent reaction.

The sensitivity of the above immunoassays is determined in part by the lower limit for detection of the label or the product of the label. In the case of luminescent or luminometric immunoassays the sensitivity of the system will depend partially on the light emitted in the luminescent reaction per unit of labelled material. It is one aim of the present invention to provide a luminescent or luminometric immunoassay with an enhanced sensitivity, achieved by determining the labelled material or the product of a label via the present improved luminescent reaction.

Whilst the present improved luminescent reaction is particularly useful in the determination of immunoassay labels or the products thereof, it is by no means limited to this use. Thus it is a further aim of the present invention to provide a luminescent or luminometric assay (immunoassay or otherwise) with an enhanced sensitivity achieved by the incorporation of the present improved luminescent reaction in the assay procedure.

Examples of assays which are not immunoassays but which may incorporate the present luminescent reaction include:
a. An elastase assay based on the release of peroxidase from an insoluble peroxidase-elastin preparation,
b. A glucose assay based on co-immobilised glucose oxidase and peroxidase, and
c. An assay of a perioxidase enzyme, a 2,3-dihydro-1,4-phthalazinedione, or an oxidant, such as hydrogen peroxide, when these materials are neither labels nor the products of labels.

According to the broadest aspect of the present invention therefore, there is provided an enhanced luminescent or luminometric assay, wherein the luminescent reaction is between a peroxidase enzyme, an oxidant, a chemiluminescent 2,3-dihydro-1,4-phthalazinedione and a sensitivity enhancer of general formula I

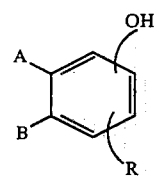

wherein R represents one or more substituent groups selected from hydrogen, halogen, keto, optionally substituted $C_1-C_6$ alkyl, optionally substituted $C_1-C_6$ alkenyl, optionally substituted aryl, optionally substituted arylazo, and optionally substituted aryloxy, optionally substituted arylthio, optionally substituted aryldisulphide, A and B, when taken separately, are the same or different and each represents a substituent group selected from hydrogen, halogen and optionally substituted $C_1-C_6$ alkyl, or, when taken together, represent

—CW=CX—CY=CZ— wherein W, X, Y and Z are the same or different and each represents a substituent group selected from hydrogen, halogen and hydroxy with the provisos, when A and B are taken separately, that R does not represent hydrogen and that the position para to the OH group is substituted, and, when A and B are taken together, that at least two of W, X, Y and Z represent hydrogen.

Preferably the assay is an immunoassay.

The present invention is based upon the surprising finding that the addition of certain readily-available phenols or naphthols to the known 2,3-dihydro-1,4-phthalazinedione/oxidant/peroxidase system, significantly enhances the sensitivity of the luminescent reaction produced.

In the present specification the term "enhanced" means that the total light emission of the present luminescent reaction and/or the signal/background ratio of the present luminescent reaction is greater than that achieved by the 2,3-dihydro-1,4-phthalazinedione/oxidant/peroxidase system in the absence of sensitivity enhancer. Only those assays that incorporate a luminescent reaction that is so "enhanced" fall within the scope of the present invention.

It is a particular advantage of the present system that enhancement produced by the addition of these phenols or naphthols is specific for reactions employing the enzyme peroxidase.

A chemiluminescent 2,3-dihydro-1,4-phthalazinedione (DPD) according to this invention may be any DPD that is converted to an excited state in a chemiluminescent reaction and then returns to a non-excited state with the emission of light.

Preferably the 2,3-dihydro-1,4-phthalazinedione is of general formula II

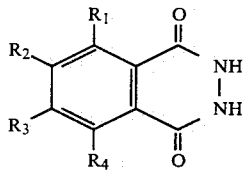

wherein $R_1$ is amino or substituted amino, and each of $R_2$, $R_3$ and $R_4$ is H, optionally substituted $C_1$–$C_6$ alkyl, optionally substituted $C_1$–$C_6$ alkenyl, hydroxyl, $C_1$–$C_6$ alkoxyl, carboxyl, amino or substituted amino, or $R_2$ is amino or substituted amino and each of $R_1$, $R_3$ and $R_4$ is H, optionally substituted $C_1$–$C_6$ alkyl, optionally substituted $C_1$–$C_6$ alkenyl, hydroxyl, $C_1$–$C_6$ alkoxyl, carboxyl, amino or substituted amino, or $R_1$ and $R_2$ are taken together and are an amino or substituted amino derivative of a benzo group, and each of $R_3$ and $R_4$ is H, optionally substituted $C_1$–$C_6$ alkyl, optionally substituted $C_1$–$C_6$ alkenyl, hydroxyl, $C_1$–$C_6$ alkoxyl, carboxyl, amino or substituted amino. Particularly preferred phthalazinediones for use in the present assay are luminol and isoluminol.

In the present specification substituted amino incorporates amido.

The form which the chemiluminescent DPD takes in the luminescent assay of the present invention will depend upon the type of assay under consideration. In the case of assays, such as organoluminescent or organoluminometric immunoassays, in which the phthalazinedione is used as a label the chemiluminescent DPD will be a substituted amino derivative of a 2,3-dihydro-1,4-phthalazonedione wherein the amino group is coupled to a ligand such as a protein, hormone, hapten, steroid, nucleic acid, metabolite, antigen or antibody. The amino group may be coupled directly to the ligand or via a bridging arm. Suitable bridging arms will be well known to those skilled in this art, as is evidenced by the discussion thereof in UK 2,008,247A and U.S. Pat. No. 4,104,029. Preferred bridging arms include those derived from hemisuccinate, hemiglutarate, hemimaleate, carboxymethyl, glucuronide, mercaptoacetate and carboxymethyl derivatives. The amino group may be coupled to the ligand by any suitable well known procedure, again certain of these procedures are discussed in UK 2,008,247A and U.S. Pat. No. 4,104,029. Preferred coupling procedures include the use of mixed anhydrides, carbodiimides and/or active esters.

Although chemiluminescent DPDs suitable for use in those assays which employ a phthalazinedione as a label may be any substituted amino derivative of a 2,3-dihydro-1,4-phthalazinedione with the amino group coupled to a ligand, the preferred substances are 5-amino-2,3-dihydro-1,4-phthalazinedione (luminol) and 6-amino-2,3-dihydro-1,4-phthalazinedione (isoluminol), in each case with the amino group coupled to a ligand, especially to an antibody.

In the case of assays other than those using phthalazinediones as labels the chemiluminescent DPD will be a 2,3-dihydro-1,4-phthalazinedione, especially of the preferred type listed above, that is not coupled to a ligand. In this case the chemiluminescent DPD may be free in solution or immobilised on a matrix. Particularly preferred materials are luminol and isoluminol.

Any phenol or naphthol of general formula I that enhances the luminescent reaction between a chemiluminescent DPD, an oxidant and a peroxidase may be used in the present assay. However the following sensitivity enhancers have been found to give particularly high levels of sensitivity enhancement, especially when the chemiluminescent DPD is luminol or isoluminol. The enhancers are 4-chlorophenol, 4-bromophenol, 4-iodophenol, 4-bromo-2-chlorophenol, 2,4-dichlorophenol, 3,4-dichlorophenol, 4-methylphenol, 4-tert.butylphenol, ethyl 3-(4-hydroxypheny)propionate, 4-benzylphenol, 4-(2',4'-dinitrostyryl)phenol, 4-hydroxycinnamic acid, 4-phenylphenol, 2-chloro-4-phenylphenol, 4-(4'-hydroxyphenyl)benzophenone, 4-(phenylazo)phenol, 4-(2'-carboxyphenylazo)phenol, 4-phenoxyphenol, 4-(4'-hydroxyphenoxy)phenol, 4-hydroxyphenyl sulphide, 4-hydroxyphenyl disulphide, naphth-2-ol, 1-bromonaphth-2-ol, 6-bromonaphth-2-ol and 1,6-dibromonaphth-2-ol. of these enhancers, 4-iodophenol, 4-phenylphenol and 2-chloro-4-phenyl-phenol are particularly effective, 4-iodophenol being the most effective.

Any peroxidase enzyme (defined as donor; hydrogen peroxide; oxidoreductase (EC No 1.11.1.7) by the Internation Union of Biochemistry) which catalyses the luminescent reaction of a 2,3-dihydro-1,4-phthalazinedione, especially luminol, in an assay may be used in the luminescent assay of the present invention. Examples include the plant peroxidases. Preferably however the enzyme will be horse radish peroxidase (EC No 1.11.1.7).

The form which the peroxidase enzyme takes in the luminescent assay of the present invention will depend upon the type of assay under consideration. In the case of assays, especially immunoassays, wherein the peroxidase is used as a label it will be coupled to a ligand such as a protein, hormone, hapten, steroid, nucleic acid, metabolite, antigen or antibody. Generally the peroxidase will be coupled to the ligand via a bridging arm. Suitable bridging arms and coupling procedures will be those described above for chemiluminescent DPDs.

In the case of assays other than those using peroxidase as a label, the enzyme will be in its free form, either in solution or immobilised on a matrix, not coupled to a ligand.

Any oxidant which reacts with a 2,3-dihydro-1,4 phthalazinedione, especially luminol or isoluminol, to cause excitation of the DPD so that it emits light in a luminescent reaction, may be used in the present luminescent reaction. Particularly preferred oxidants are perborate ion and hydrogen peroxide.

In assays, especially immunoassays, which employ a 2,3-dihydro-1,4-phthalazinedione, or a peroxidase enzyme as a label for a ligand, a known quantity of the oxidant will be added to the reaction mixture, generally from a proprietary source. In certain other assays however, the amount of oxidant, generally hydrogenperoxide, present will be unknown. In this second type of assay the label will be a substance, often an enzyme such as glucose oxidase, which participates in the conversion of a substrate into the oxidant. Thus, in this case, the present luminescent reaction will be used to determine the quantity of labelled ligand by the measurement of the oxidant concentration in the luminescent reaction mixture.

Light emission from the luminescent assay of the present invention, although depending primarily on the choice of peroxidase, oxidant, sensitivity enhancer and chemiluminescent DPD, will also be determined by secondary factors such as temperature pH, reagent concentration, mixing speed and method of light measurement. To maximise the sensitivity of the present system these secondary factors should be adjusted to obtain the maximum light emission, in a reproducible and easily measurable manner, with the signal to background ratio as high as possible.

The conditions chosen are generally a compromise involving the enzyme or catalytic activity of the peroxidase, the kinetics of the reaction, the apparatus employed, the signal to background ratio and the sensitivity required.

The present inventors have found that in order to achieve optimum results the present luminescent reaction should be conducted under moderate conditions of temperature, ranging from 10° to 50° C., and pH, in the range of 6 to 10, most often between 7 and 9. Suitable buffering substances for the method of the present invention are phosphate, tris(hydroxymethyl)aminomethane, 2-amino-2-methyl-1,3-propanediol, acetate, carbonate and borate.

Generally, the concentrations of the reagents in the luminescent reaction mixture, with the exception of the material to be determined, are kept constant. The variable factor may be, for example, the concentration of a labelled ligand, a product of a label, on oxidant or unbound peroxidase.

The following reagent concentrations are particularly suitable for use in the present luminescent reaction:
  peroxidase: 0.1 $\mu$g–5000 mg/liter
  oxidant: 10 $\mu$mol–300 mmol/liter
  chemiluminescent DPD: 0.5 $\mu$mol–200 mmol/liter
  sensitivity enhancer: 1 $\mu$mol–100 mmol/liter In performing the present luminescent reaction, certain of the four essential reagents (but omitting at least one) are placed in a sample tube. The luminescent reaction is then triggered by the addition, to the tube, of the missing essential reagent(s). The light emitted may be quantified by a standard measuring device, such as a photomultiplier tube, the signal from which is fed to and displayed or recorded on a recorder, oscilliscope or scalar. The light may also in some cases be observed by the naked eye or recorded on a photographic plate. Preferably however the light is quantified on a luminometer of the type described in UK Patent Application No. 2025609A.

The luminescent assay of the present invention may be used in three major types of immunoassay, the distinguishing feature of each being the type of label attached to the ligand. The labels are,
  a. an amino or a substituted amino derivative of a 2,3-dihydro-1,4-phthalazinedione, wherein the amino group is coupled to the ligand,
  b. a peroxidase enzyme, and
  c. a substance, other than those listed under a and b and generally an enzyme such as glucose oxidase, which participates in the conversion of a substrate to a material which may be determined by the present luminescent reaction (generally hydrogen peroxide or peroxidase).

In the above immunoassays labelling of the substance to be assayed or of an antibody to such a substance is possible. Depending on the type of label employed, the assay may be either heterogeneous or homogenous. In the former case complex fluids such as serum may be analysed, however, in the latter case, a preliminary extraction or purification step may be necessary.

Typical heterogeneous and homogeneous luminescent or luminometric immunoassays are outlined below:

1. HETEROGENEOUS LUMINESCENT OR LUMINOMETRIC IMMUNOASSAY

In this type of immunoassay the substance to be assayed is reacted with an antibody thereto. The free antibody is then separated from the bound antibody. The reaction is quantified by labelling either the antibody, the substance to be assayed or another molecule which can react with the free or bound moieties after separation.

2. COMPETITIVE HETEROGENEOUS LUMINESCENT IMMUNOASSAY

In this case an unknown amount of the substances to be assayed is mixed with a known amount of said substance coupled with a label and a known, but limited, amount of an antibody thereto. A competitive reaction between the labelled and unlabelled substance for the antibody ensues. The complexes between antibody and unlabelled substance and between antibody and labelled substance are separated from the free labelled and unlabelled substance.

The amount of labelled substance bound to antibody is related to the amount of unlabelled substance in the solution being assayed. These quantities may be determined either by measuring the amount of label bound to antibody or by measuring the amount of free labelled substance remaining. Examples of this type of assay wherein peroxidase is the label and the antibody is bound to a solid phase, viz the walls of a glass test tube, are given in UK 2,044,927A.

3. "TWO-SITE" HETEROGENEOUS LUMINOMETRIC IMMUNOASSAY

In this type of immunoassay the substance to be assayed is first bound to an unlabelled antibody thereto which in turn is bound to a solid phase support, such as plastic. The complex (between antibody and substance) is then treated with a labelled antibody. Analysis for the labelled antibody in the solid complex obtained may then be effected by separating the solid complex from the solution, and then determining either the amount of label present in the separated solid complex or the amount of label present in the residual labelled antibody dissolved in the solution.

In alternative embodiments of this type of immunoassay the substance to be assayed may either be bound consecutively to the labelled antibody and to the unlabelled, solid supported antibody or be bound to both the labelled and unlabelled antibody in one binding step.

4. HOMOGENEOUS LUMINESCENT OR LUMINOMETRIC IMMUNOASSAY

This is applicable to immunoassays wherein the label is an amino or a substituted amino derivative of a 2,3-dihydro-1,4-phthalazinedione. It depends upon the light emitted from the free labelled substance of interest (or antibody thereto) being of a different intensity or wavelength to the light emitted from the bound labelled substance of interest (or antibody thereto).

In one example it was found that the intensity of light emitted from the reaction of a (progesterone-isoluminol deriv) conjugate, a haem catalyst and hydrogen peroxide was of a lower intensity than the same reaction performed in the presence of anti-progesterone IgG.

Thus in the assay an unknown progesterone sample was first incubated with a known amount of anti-progesterone IgG. After equilibrium was reached a known amount progesterone-isoluminol deriv conjugate was added, followed by a known amount of haem and hydrogen peroxide. The light emitted was measured and the amount of progesterone present in the unknown sample thereby determined from the standard curve. (The more progesterone present in the unknown sample, the less free IgG is left at equilibrium and the lower is the light yield of the luminescent reaction).

In this way the determination of progesterone may be achieved without the requirement of a separation step.

In all of the above immunoassays the quantifying, detecting or locating step may be the luminescent reaction of the present invention.

The antibodies employed in the above immunoassays may be purchased commercially or prepared by known immunological techniques. The antibodies may be in the form of a complex mixture of antibodies or they may be one or more monoclonal antibodies. Only a small volume of antibody is generally required and it is maintained at the conditions of pH, ionic strength and temperature appropriate for its activity.

Antibodies to the following non-exhaustive list of substances may be usefully employed in immunoassays utilising the present luminescent reaction: proteins such as insulin, alphafetoprotein and ferritin, hormones such as growth hormone, parathyroid hormone, follicle stimulating hormone, luteinising hormone, thyroid stimulating hormone, adrenocorticotrophic hormone, glucagon, prolactin and calcitonin, haptens/steroids such as estriol, progesterone and cortisol, drugs such as digoxin, antigens such as cell surface antigens and carcino embryonic antigen and antibodies such as mumps virus antibody, human immunoglobulin G (IgG), rabbit IgG, sheep IgG, guinea pig IgG, donkey IgG and human immunoglobulins E and M.

The luminescent assay of the present invention may also be used in assays other than the immunoassays described above. These include:

1. THE ASSAY OF ELASTASE BASED ON THE RELEASE OF PEROXIDASE FROM AN INSOLUBLE PEROXIDASE ELASTIN PREPARATION

In this assay a solid elastin-peroxidase conjugate is incubated with varying amounts of the enzyme elastase. After a predetermined period unreacted conjugate is removed by centrifugation and the supernatant is assayed for unbound peroxidase.

The amount of unbound peroxidase present in the supernatant is related to the elastase activity in the sample tested.

2. THE ASSAY OF PROTEINASE BASED ON THE RELEASE OF ISOLUMINOL FROM A SYNTHETIC PEPTIDE SUBSTRATE

In this assay immobilised synthetic peptide substrate, Affigel 10-Ala-Ala-Ala-Phe-isoluminol, is treated with varying quantities of proteinase. After a predetermined period unreacted substrate is removed by centrifugation and the supernatant is assayed for isoluminol. The amount of isoluminol present in the supernatant is related to proteinase activity in the sample tested.

3. THE ASSAY OF GLUCOSE BASED ON CO-IMMOBILISED GLUCOSE OXIDASE AND PEROXIDASE

In this assay glucose oxidase and peroxidase are co-immobilised on a support, eg Sepharose or plastic tubes. To this is added a solution of luminol and sensitivity enhancer. Finally a solution of glucose is added and the light emission recorded. Light emission is directly related to the amount of glucose in solution.

The major use of the present assay will be in clinical laboratories or doctors' surgeries. It is usual for such laboratories and/or surgeries to obtain the materials to be used in a given assay procedure in the form of an assay kit.

Accordingly the present invention also provides an assay kit for use in the enhanced luminescent or luminometric assay of the present invention comprising:

a. a peroxidase enzyme,
b. a sensitivity enhancer of general formula I, wherein R, A and B are as defined above, and
c. a chemiluminescent 2,3-dihydro-1,4-phthalazinedione.

The test kit may also contain an oxidant, but in many cases this material may either be provided separately or be the substance to be assayed.

Preferably the peroxidase enzyme, the oxidant, the sensitivity enhancer and the chemiluminescent DPD will each be one of those substances listed above as preferred for use in the present assay. In one particularly preferred embodiment of the present assay kit at least one of the peroxidase enzyme and the chemiluminescent DPD is coupled to an antibody to the substance to be assayed.

Optionally the assay kit may also contain one or more standard solutions each containing a known amount of the substance to be assayed, and/or one or more of the preferred buffer solutions. Conveniently the assay kit may also include a reaction vessel suitable for use in conjunction with the apparatus used for the determination of the light emitted in the course of carrying out the assay. Also a mixing device may be included in the assay kit, for use in ensuring adequate admixture of the reagents.

The assay and assay kit of the present invention will now be described by way of example only.

MATERIALS AND METHODS

Reagents

Horse radish peroxidase (HRP: Reinheit Zahl (the ratio of optical density at 403 nm to that at 250 mm; RZ) approximately 1.0) was obtained from Hughes and Hughes Ltd., Romford, Essex and was purified by gel filtration using a 2.6 cm × 40 cm Ultrogel AcA 34 column (LKB Instruments Ltd, South Croydon, Surrey). The column was eluted using 0.015 mol/l phosphate buffer, pH 7.2, containing 0.15 mol/l NaCl; the purified peroxidase obtained had an RZ of approximately 3.0.

Alpha-fetoprotein (AFP), rabbit anti-human AFP (code 100-008) and rabbit anti-human AFP/HRP conjugate were obtained from Dako Products, Mercia Brocades Ltd, Brocades House, Pyrford Road, West Byfleet, Weybridge, Surrey.

Thyroxine (T4), rabbit anti-T4 coated tubes and T4/HRP conjugate were obtained from the Boehringer Corporation, Lewes, Sussex, UK.

Rubella virus (human) coated beads and anti-human IgG (goat)/HRP conjugate were obtained from Abbott Laboratories Ltd, Diagnostic Division, Brighton Hill Parade, Basingstoke, Hampshire.

Anti-IgE (goat) coated tubes and anti-IgE (rabbit) peroxidase conjugate were obtained from Behringwerke AG, Marburg.

Luminol (5-amino-2,3-dihydro-1,4-phthalazinedione) and isoluminol (6-amino-2,3-dihydro-1,4-phthalazinedione) were obtained from the Sigma Chemical Co, Fancy Road, Poole, Dorset, UK. The mono-sodium salt of luminol was prepared as described previously (Ham et al, Anal Lett, 1979, 12, 535).

7-Dimethylaminonaphthalene-1,2-dicarboxylic acid hydrazide (formula II, $R_1$ and $R_2$ are taken together and are a dimethylamino substituted benzo group, $R_3 = R_4 = H$) was obtained from Boehringer Mannheim.

N-(6-Aminohexyl)-N-ethyl isoluminol was obtained from LKB Finland.

All of the phenols and naphthols were obtained from the Aldrich Chemical Co, except for 2-chlorophenol and 2,4,6-trichlorophenol (obtained from Fluka AG, Chemische Fabrik, CH 9470, Buchs, Switzerland), 2-naphthol (obtained from BDH Chemicals Ltd, Atherstone, Warwickshire) and 4-hydroxyphenyl sulphide (obtained from Fluorochem Ltd, Glossop, Derbyshire).

Elastin, elastase, and glucose oxidase were obtained from the Sigma Chemical Co, Dorset.

Analytical Equipment

Chemiluminescent reactions were carried out in 10 mm × 10 mm, 4 ml volume plastic disposable cuvettes (W Sarstedt Ltd, Leicester LE3 1UQ, UK). The light emitted was quantitated via a luminometer described previously (Carter et al, UKPA 2025609A), incorporating a modification allowing several cuvettes to be successively positioned, accurately and reproducibly, in front of the photocathode of the photomultiplier tube.

Results were displayed on a fast potentiometric chart recorder (Type PM 8202; Philips Eindhoven, Netherlands; full scale deflection time, less than 0.25 sec).

EXAMPLE 1

Luminescent assay of peroxidase using luminol and 4-iodophenol

Sodium luminol (50 mg) and hydrogen peroxide (62 $\mu$l, 30% w/v) were added to 200 ml Tris buffer (0.1 Molar, pH 8.5). The solution was prepared several hours before use and used to initiate the luminescent reaction. 10 $\mu$l of 4-iodophenol in dimethyl sulphoxide (4.54 m mole/liter) was placed in one corner of a cuvette and 10 $\mu$l of rabbit anti AFP-HRP conjugate 1:1000 dilution) was placed in another corner. The reaction was initiated by injection of the luminol/$H_2O_2$ reagent (0.9 ml). The light output was measured and is given in Table 1. The improvement in signal/background ratio was also measured and is given in Table 2.

EXAMPLES 2-3

The procedure of Example 1 was repeated except that the amount of 4-iodophenol solution added was increased to 20 $\mu$l and 90 $\mu$l respectively. The light output was measured and is given in Table 1. The improvement in signal/background ratio was also measured and is given in Table 2.

EXAMPLES 4-8

The procedure of Example 1 was repeated except that 4-iodophenol was replaced by the following sensitivity enhancers:
4-Bromophenol
4-Chlorophenol
4-Bromo-2-chlorophenol
2,4-Dichlorophenol
3,4-Dichlorophenol
Results are given in Tables 1 and 2.

EXAMPLES 9-13

The procedure of Examples 4 to 8 were repeated except that the amount of sensitivity enhancer solution added was increased to 90 $\mu$l. Results are given in Tables 1 and 2.

EXAMPLES 14-18

The procedure of Example 1 was repeated except that 4-iodophenol was replaced by the following sensitivity enhancers:
4-Hydroxycinnamic acid
2-Naphthol
6-Bromonaphth-2-ol
4-Styrylphenol
4-(4-Hydroxyphenyl)phenol
Results are given in Tables 1 and 2.

EXAMPLES 19-21

The procedure of example 1 was repeated except that the 10 $\mu$l of 4-iodophenol was replaced by 5 $\mu$l of the following sensitivity enhancers:
4-Phenylphenol
1,6-Dibromonaphth-2-ol
1-Bromonaphth-2-ol
Results are given in Tables 1 and 2

EXAMPLES 22-26

The procedure of Example 1 was repeated except that the 10 $\mu$l of 4-iodophenol was replaced by 5 $\mu$l of the following sensitivity enhancers:
4-Hydroxyphenyl sulphide 4-Hydroxyphenyl disulphide
4-(2′,4′-Dinitrostyryl)phenol
4-(4′-Hydroxyphenyl)benzophenone
4-(4′-Hydroxyphenoxy)phenol The improvement in signal/background ratio was measured and is given in Table 3.

EXAMPLES 27–30

The procedure of Example 1 was repeated except that 10 μl of 4-iodophenol was replaced by 20 μl of the following sensitivity enhancers:
4-(Phenylazo)phenol
4-(2′-Carboxyphenylazo)phenol
4-Benzylphenol
Ethyl 3-(4-Hydroxyphenyl)propionate The improvement in signal/background ratio was measured and is given in Table 3.

COMPARATIVE EXAMPLE

The procedure of Example 1 was repeated except that no sensitivity enhancer was added to the luminescent reaction mixture. Results are given in Tables 1, 2 and 3.

TABLE 1

Enhancement of Light Emission by Various Phenols and Naphthols

| Example | Enhancer | Volume Added (μl) | Light Emission (mV 700 Volts PM) |
|---|---|---|---|
| Comparative | — | — | 11 |
| 1 | 4-Iodophenol | 10 | 903 |
| 2 | 4-Iodophenol | 20 | 1958 |
| 3 | 4-Iodophenol | 90 | 3056 |
| 4 | 4-Bromophenol | 10 | 261 |
| 5 | 4-Chlorophenol | 10 | 190 |
| 6 | 4-Bromo-2-chlorophenol | 10 | 80 |
| 7 | 2,4-Dichlorophenol | 10 | 29 |
| 8 | 3,4-Dichlorophenol | 10 | 20 |
| 9 | 4-Bromophenol | 90 | 1379 |
| 10 | 4-Chlorophenol | 90 | 1190 |
| 11 | 4-Bromo-2-chlorophenol | 90 | 555 |
| 12 | 2,4-Dichlorophenol | 90 | 165 |
| 13 | 3,4-Dichlorophenol | 90 | 82 |
| 14 | 4-Hydroxycinnamic acid | 10 | 2317 |
| 15 | 2-Naphthol | 10 | 50 |
| 16 | 6-Bromonaphth-2-ol | 10 | 42 |
| 17 | 4-Styrylphenol | 10 | 11 |
| 18 | 4-(4-Hydroxyphenyl) phenol | 10 | 9 |
| 19 | 4-Phenylphenol | 5 | 5830 |
| 20 | 1,6-Dibromonaphth-2-ol | 5 | 2401 |
| 21 | 1-Bromonaphth-2-ol | 5 | 651 |

NB: Light emission is measured as output (mV) at a photomultiplier voltage of 700 volts.

TABLE 2

| Example | Improvement in Signal/Background Ratio |
|---|---|
| Comparative | 1 |
| 1 | 170 |
| 2 | 510 |
| 3 | 1697 |
| 4 | 40 |
| 5 | 25 |
| 7 | 7 |
| 8 | 4 |
| 9 | 476 |
| 10 | 357 |
| 12 | 258 |
| 13 | 44 |
| 14 | 2935 |
| 15 | 1698 |
| 16 | 1268 |
| 17 | 187 |
| 18 | 54 |
| 19 | 3482 |
| 20 | 2055 |
| 21 | 3931 |

TABLE 3

| Example | Enhancer | Volume Added (μl) | Improvement in Signal/Background Ratio |
|---|---|---|---|
| Comparative | — | — | 1 |
| 22 | 4-Hydroxyphenylsulphide | 5 | 73 |
| 23 | 4-Hydroxyphenyldisulphide | 5 | 1724 |
| 24 | 4-(2′,4′-Dinitrostyryl) phenol | 5 | 73 |
| 25 | 4-(4′-Hydroxyphenyl) benzophenone | 5 | 118 |
| 26 | 4-(4′-Hydroxyphenoxy) phenol | 5 | 521 |
| 27 | 4-(Phenylazo) phenol | 20 | 659 |
| 28 | 4-(2′-Carboxyphenylazo) phenol | 20 | 171 |
| 29 | 4-Benzylphenol | 20 | 109 |
| 30 | Ethyl 3-(4-hydroxyphenyl) propionate | 20 | 86 |

EXAMPLE 31–43

The procedure of Example 1 was repeated except that 4-iodophenol was replaced by various alternative phenols and naphthols (10 μl, 1 mg/ml solution in DMSO). The light output was compared to the light output of a luminescent reaction without enhancer. If light output was greater in the presence of the phenol or naphthol than in its absence, the luminescent reaction was said to be enhanced. Results are given in Table 4.

TABLE 4

Effect of Various Phenols and Naphthols on Light Output

| Example | Phenol/Naphthol | Enhancement |
|---|---|---|
| 31 | 2,3,4-Trichlorophenol | Yes |
| 32 | 4-Chloro-2-methylphenol | Yes |
| 33 | 4-Chloro-3-methylphenol | Yes |
| 34 | 4-Chloro-3,5-dimethylphenol | Yes |
| 35 | 4-Bromo-3,5-dimethylphenol | Yes |
| 36 | 4-Methylphenol | Yes |
| 38 | 3,4-Dimethylphenol | Yes |
| 39 | 4-Tert. butylphenol | Yes |
| 40 | 4-(3′-Methylcrotyl) phenol | Yes |
| 41 | Alpha-cyano-4-hydroxycinnamic acid | Yes |
| 42 | 4-Phenoxyphenol | Yes |
| 43 | 2,7-Dihydroxynaphthol | Yes |

EXAMPLE 44

The procedure of Example 1 was repeated except that N-(6-aminohexyl)-N-ethylisoluminol replaced luminol.

EXAMPLE 45

The procedure of Example 1 was repeated except that luminol was replaced by isoluminol.

EXAMPLE 46

The procedure of Example 1 was repeated except that luminol was replaced by 7-dimethylamino naphthalene-1,2-dicarboxylic acid hydrazide (9-dimethylamino-2,3-dihydrobenzo[f]phthalazine-1,4-dione) and the phthalazinedione/$H_2O_2$ was diluted 1 in 10 before use.

EXAMPLE 47

The procedure of Example 1 was repeated except that hydrogen peroxide was replaced by sodium perborate.

EXAMPLE 48

Assay of Alphafeto protein (AFP)

a. Coating polystyrene beads with anti-AFP
(1) To a 500 ml wide mouthed glass bottle was added 125 ml glycine/NaOH buffer (0.1 mol/l, pH8.8) and 0.25 g BSA. The solution was then mixed for 2 hrs on a roller mixer at 20° C. After this time the bottle (and its lid) was rinsed with glycine buffer (3×50 ml) to remove any unbound albumin and finally was allowed to drain.
(2) 1000 Polystyrene beads were washed with Lipsol (Trade Mark, 1%, 500 ml) for 30 min. After washing with distilled water the beads were placed in a Buchner flask, together with 200 ml glycine buffer, and degassed.
(3) Glycine buffer (400 ml) was transferred to the precoated glass bottle and rabbit anti-human AFP (1.5 ml) was added. The solution was well mixed and then the degassed beads were added. The whole was mixed on the roller mixer for 6 hrs at 20° C.
(4) After 6 hrs the glycine buffer-antibody solution was decanted and the beads were washed twice with 400 ml PBS (0.015 mol/l phosphate, 0.15 mol/l NaCl, pH7.2). After decanting the second PBS wash, a solution of BSA (0.5%) in PBS (400 ml) was added. Once again the whole was mixed on the roller mixer at 20° C. After 30 min the PBS-albumin solution was removed and acetate buffer (0.1 mol/l, pH4.2, 400 ml) containing Tween 20 (Trade Mark, 0.01%) was added. Mixing was effected for 10 min and then the acetate buffer was replaced by PBS buffer containing 0.05% Tween (2×400 ml). Finally the PBS was decanted and the beads were dried on filter paper at 20° C. for 30 min. The beads were stored in screw capped bottles at 4° C.

b. (1) Sufficient antibody coated beads (step a. above) in PBS were degassed for 15–30 mins.
(2) 50 µl of a specimen containing AFP was added to a cuvette together with 0.95 ml PBS/BSA/Tween (phosphate 0.015 mol/l; Nacl 0.15 mol/l; BSA 0.2%; Tween 20.0.05%; pH 7.2). The solution was warmed to 37° C. and then incubated with the beads for 1 hr.
(3) The solution was then decanted and the beads were washed with PBS/Tween (200 ml for 15 sec, then 200 ml for 5 min).
(4) The beads were then incubated with 0.9 ml 1:1000 dilution of rabbit anti-human AFP/HRP conjugate for 1 hr. (The conjugate was diluted in PBS/BSA/Tween and, prior to addition to the beads, was warmed to 37° C.).

c (1) The solution was once again decanted and the beads were washed with deionised, distilled water for 2 min. After decanting the water the beads were carefully transferred to curvettes (one per cuvette).
(2) Into the corner of each cuvette was also placed 10 µl of 4-iodophenol (1 mg/ml) in Tris buffer (0.1 mol/l, pH 8.0). The lminescent reaction was initiated by the injection of 0.9 ml luminol/$H_2O_2$ solution (sodium luminol (50 mg), $H_2O_2$ (62 µl; 30% w/v), Tris (0.1 mol/l, pH 8.0, 200 ml). The light emission after 30 sec was measured and compared with a previously prepared standard curve to determine AFP concentration.

EXAMPLE 49

Assay of T4

T4 was assayed using a competitive enzyme linked immunosorbent assay. A mixture of specimen containing unlabelled T4 and T4/HRP conjugate was incubated with tubes coated with a limited quantity of anti-T4 (rabbit).

After equilibrium had been reached unbound material was washed from tubes and 10 µl of 4-iodophenol (1 mg/ml) in Tris buffer (0.1 mol/l), pH 8.0) was placed into each tube. The luminescent reaction was initiated by the injection of 0.9 ml luminol/$H_2O_2$ solution (sodium luminol (50 mg) $H_2O_2$ (62 µl; 30% w/v), Tris (0.1 mol/l, pH 8.0, 200 ml). The light emission after 30 sec was measured and compared with a previously prepared standard curve to determine T4 concentration.

EXAMPLE 50

Assay of anti-rubella IgG

A test specimen containing anti-rubella IgG was incubated with rubella virus (human) coated beads in Tris buffer. After washing to remove unreacted components the beads were incubated with antihuman IgG (goat)/HRP conjugate, again in Tris buffer.

The solution was decanted and the beads were washed with deionised, distilled water. After removing the washed beads from the water they were transferred to cuvettes (one per cuvette).

Into the corner of each cuvette was also placed 10 µl of 4-iodophenol (1 mg/ml) in Tris buffer (0.1 mol/l, pH 8.0). The luminescent reaction was initiated by the injection of 0.9 ml luminol/$H_2O_2$ solution (sodium luminol (50 mg), $H_2O_2$ (62 µl; 30% w/v), Tris (0.1 mol/l, pH 8.0, 200 ml). The light emission after 30 sec was measured and compared with a previously prepared standard curve to determine anti-rubella IgG concentration.

EXAMPLE 51

Assay of IgE

A specimen containing known IgE was added to anti-IgE (goat) coated tubes and incubated for 2 hr at 20° C. After this time the tubes were washed to remove unreacted components and a known quantity of anti-IgE (rabbit) peroxidase conjugate was added to the tubes and incubated for a further 2 hr at 20° C. The excess enzyme-conjugated antibodies were then washed out and the bound enzyme activity determined as follows:

Into the corner of each tube was placed 10 µl of 4-iodophenol (1 mg/ml) in Tris buffer (0.1 mol/l, pH 8.0). The luminescent reaction was initiated by injection of 0.9 ml luminol/H$_2$O$_2$ (luminol (50 mg), H$_2$O$_2$ (62 μl, 30% w/v), Tris (0.1 mol/l, pH 8.0, 200 ml). The light emission after 30 sec was measured and compared with a previously prepared standard curve to determine IgE concentration.

EXAMPLE 52

Assay of elastase

Horseradish peroxidase was conjugated to powdered elastin by the method of G C Saunders et al., Anal Biochem, 1982, 126, 122. 1 ml of elastin peroxidase suspension was washed and equilibrated in 2 ml of 0.01 mol/l Tris buffer (pH 9), containing CaCl$_2$ (2 mmol/l) for 0.5 hr at 37° C. The conjugate was centrifuged and the supernatant discarded. Varying amounts of elastase (0-100 ng/ml) in Tris-CaCl$_2$ buffer were added and incubated at 37° C. with the elastin-HRP. After 60 mins unreacted elastin-HRP was removed by centrifugation and an aliquot of supernatant transferred and recentrifuged. 200 μl of supernatant was removed and placed in a cuvette and light emission was initiated by the addition of 0.9 ml luminol/H$_2$O$_2$/4-iodophenol solution (sodium luminol (50 mg), H$_2$O$_2$ (62 μl; 30% w/V), 4-iodophenol (2 ml, 1 mg/ml in DMSO), in 200 ml Tris buffer (0.1 mol/l, pH 8.0). The light emission after 30 sec was measured.

EXAMPLE 53

Glucose assay based on co-immobilised glucose oxidase and peroxidase

Glucose oxidase (5 mg; Sigma) and horseradish peroxidase (5 mg, Sigma) were co-immobilised onto cyanogen bromide activated Sepharose (Pharmacia, UK) by the procedure of Ford and DeLuca, Anal. Biochem, 1981, 110, 43. The immobilised enzymes were suspended in phosphate buffer (0.1 mol/l, ph 7.0). A suspension of the immobilized enzymes (100 gm/l, 50 μl) were added to 1 ml of aqueous luminol solution (25 mg per 100 ml) and 50 μl of 4-iodophenol (1 mg/ml in DMSO) contained in a cuvette. A 10 μl aqueous sample of a glucose containing solution was then added, the cuvette contents mixed, and the light emission recorded. Peak light emission was linear between 50 and 500 nmol of glucose. Alternatively the glucose oxidase and peroxidase can be immobilised onto the surface of plastic supports (eg Leon et al, Clin Chem, 1977, 23, 1556).

We claim:

1. In a luminescent or luminometric assay which comprises carrying out a chemiluminescent reaction between a peroxidase enzyme, an oxidant, and a chemiluminescent 2,3-dihydro-1,4-phthalazinedione and measuring or detecting the chemiluminescence thereby produced, the improvement wherein the reaction is carried out in the presence of a phenolic compound of the formula:

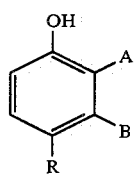 (1)

wherein:

(i) A and B are hydrogen; and
R is halogen;
phenyl;

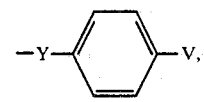

being —CH$_2$—, —O— or —N=N— and V being hydrogen or Y being —O—, —S— or —S—S— and V being hydroxy;

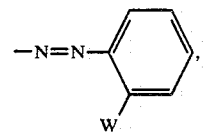

W being hydrogen or carboxy;

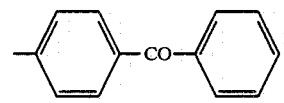

—CH=CH—Z, Z being carboxy or 2,4-dinitrophenyl;
—CH$_2$CH$_2$COOC$_2$H$_5$; or C$_1$-C$_6$ alkyl;
(ii) A is hydrogen;
B is halogen or C$_{1-6}$ alkyl; and
R is halogen;
(iii) A is halogen;
B is hydrogen; and
R is halogen or phenyl; or
(iv) A is hydrogen or halogen;
R and B together represent a naphthalene nucleus-completing chain which, read in the direction from R to B, is of formula

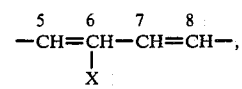

X being hydrogen or halogen, whereby the compound of formula (1) is a beta-naphthol of formula:

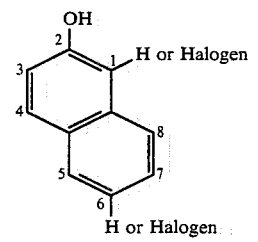

and "halogen" in every occurrence in (i) through (iv) above means chlorine, bromine or iodine.

2. An assay according to claim 1 wherein the chemiluminescent 2,3-dihydro-1,4-phthalazinedione falls within the general formula (2)

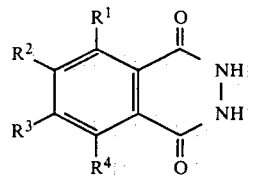

(2)

wherein $R^1$ is substituted or unsubstituted amino, and each of $R^2$, $R^3$ and $R^4$ is H, substituted or unsubstituted $C_1$-$C_6$ alkyl, substituted or unsubstituted $C_1$-$C_6$ alkenyl, hydroxy, $C_1$-$C_6$ alkoxyl, carboxyl, or substituted or unsubstituted amino, or $R^2$ is substituted or unsubstituted amino and each of $R^1$, $R^3$ and $R^4$ is H, substituted or unsubstituted $C_1$-$C_6$ alkyl, substituted or unsubstituted $C_1$-$C_6$ alkenyl, hydroxyl, $C_1$-$C_6$ alkoxyl, carboxyl, or substituted or unsubstituted amino, or $R^1$ and $R^2$ are taken together and are a substituted or unsubstituted amino derivative of a benzo group and each of $R^3$ and $R^4$ is H, substituted or unsubstituted $C_1$-$C_6$ alkyl, substituted or unsubstituted $C_1$-$C_6$ alkenyl, hydroxyl, $C_1$-$C_6$ alkoxyl, carboxyl, or substituted or unsubstituted amino.

3. An assay according to claim 1, wherein the chemiluminescent 2,3-dihydro-1,4-phthalazinedione is luminol or isoluminol.

4. An assay according to claim 1, wherein the peroxidase enzyme is horseradish peroxidase.

5. An assay according to claim 1 wherein the oxidant is hydrogen peroxide or perborate ion.

6. An assay according to claim 1, wherein the peroxidase enzyme is present in a free or ligand-coupled form and the presence or the amount of peroxidase enzyme is deduced from the detection or measurement, respectively, of the chemiluminescence.

7. An assay according to claim 1 wherein the phenolic compound is 4-iodophenol, 4-phenylphenol or 2-chloro-4-phenylphenol.

8. An assay according to claim 1, wherein the 2,3-dihydro-1,4-phthalazinedione is luminol or isoluminol, the oxidant is hydrogen peroxide, the phenolic compound is 4-iodophenol and the peroxidase enzyme is horseradish peroxidase in ligand-coupled form, and the presence or the amount of horseradish peroxidase is deduced from the detection or measurement respectively, of the chemiluminescence.

9. A kit for use in a luminescent or luminometric assay comprising the following components in separate containers:
 a chemiluminescent 2,3-dihydro-1,4-phthalazinedione,
 a peroxidase enzyme, and
 a phenolic compound defined in claim 1.

10. A kit according to claim 9 wherein the chemiluminescent 2,3-dihydro-1,4-phthalazinedione falls within the general formula (2):

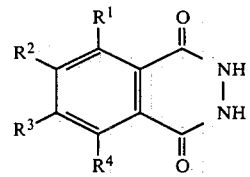

(2)

wherein $R^1$ is substituted or unsubstituted amino, and each of $R^2$, $R^3$ and $R^4$ is H, substituted or unsubstituted $C_1$-$C_6$ alkyl, substituted or unsubstituted $C_1$-$C_6$ alkenyl, hydroxyl, $C_1$-$C_6$ alkoxy, carboxyl, or substituted or unsubstituted amino, or $R^2$ is substituted or unsubstituted amino and each of $R^1$, $R^3$ and $R^4$ is H, substituted or unsubstituted $C_1$-$C_6$ alkyl, substituted or unsubstituted $C_1$-$C_6$ alkenyl, hydroxyl, $C_1$-$C_6$ alkoxy, carboxyl, or substituted or unsubstituted amino, or $R^1$ and $R^2$ are taken together and are a substituted or unsubstituted amino derivative of a benzo group and each of $R^3$ and $R^4$ is H, substituted or unsubstituted $C_1$-$C_6$ alkyl, substituted or unsubstituted $C_1$-$C_6$ alkenyl, hydroxyl, $C_1$-$C_6$ alkoxyl, carboxyl, or substituted or unsubstituted amino.

11. A kit according to claim 9, wherein the chemiluminescent 2,3-dihydro-1,4-phthalazinedione is luminol or isoluminol.

12. A kit according to claim 9, wherein the peroxidase enzyme is horseradish peroxidase.

13. A kit according to claim 9, wherein the peroxidase enzyme is present in a free or ligand-coupled form.

14. A kit according to claim 9 wherein the phenolic compound is 4-iodophenol, 4-phenylphenol or 2-chloro-4-phenylphenol.

15. A kit according to claim 9, wherein the 2,3-dihydro-1,4-phthalazinedione is luminol or isoluminol, the peroxidase enzyme is horseradish peroxidase and is present in ligand-coupled form and the phenolic compound is 4-iodophenol.

* * * * *

UNITED STATES PATENT AND TRADEMARK OFFICE
CERTIFICATE OF CORRECTION

PATENT NO. : 4,598,044

DATED : July 1, 1986

INVENTOR(S) : KRICKA et al

Page 1 of 2

It is certified that error appears in the above-identified patent and that said Letters Patent is hereby corrected as shown below:

Column 1, line 12, delete "istopes" and replace by --isotopes--

Column 1, line 37 delete "emulsion" and replace by --emission--

Column 1, line 38 delete " product" and replace by --produce--

Column 4, line 7 delete "," and replace by --;--

Column 4, line 37 delete "(4-hydroxypheny)" and replace by --(4-hydroxyphenyl)--

Column 4, line 45 delete "2-ol, of" and replace by --2-ol. Of--

Column 5, lines 16 and 17 delete "hydrogenperoxide," and replace by --hydrogen peroxide,--

Column 5, line 54 delete "on" and replace by --an--

Column 6 line 26 delete "analysed," and replace by --analysed;--

Column 11, line 39 delete "Tables 1 2" and replace by --Tables 1, 2--

UNITED STATES PATENT AND TRADEMARK OFFICE
CERTIFICATE OF CORRECTION

PATENT NO. : 4,598,044

DATED : July 1, 1986

INVENTOR(S) : KRICKA et al

It is certified that error appears in the above-identified patent and that said Letters Patent is hereby corrected as shown below:

Column 13, line 59 delete "Nacl" and replace by --NaCl--

Column 13 line 60 delete "20 0.05%;" and replace by --20,0.05%;--

Column 14, line 9 delete "lminescent" and replace by --luminescent--

Column 15, line 38 delete "ph" and replace by --pH--

Column 16, line 11 delete "being $-CH_2-$," and replace by --Y being $-CH_2-$,--

Column 16, line 45 delete "$-\overset{5}{C}H=\overset{6}{C}H-\overset{7}{C}H=\overset{8}{C}H-$," and replace by --$-\overset{5}{C}H=\underset{X}{\overset{6}{C}}-\overset{7}{C}H=\overset{8}{C}H-$,--

Signed and Sealed this

Twenty-third Day of December, 1986

*Attest:*

DONALD J. QUIGG

*Attesting Officer*   *Commissioner of Patents and Trademarks*